United States Patent [19]

Schwartz et al.

[11] 4,306,554
[45] Dec. 22, 1981

[54] ISOLATION STORAGE AND INTERMIXING SYRINGE FOR MEDICANTS

[76] Inventors: Boris Schwartz, 625 Lafayette Ave., Hawthorne, N.J. 07506; Cyril H. T. Woodward, 160 Howard Ave., Rochelle Park, N.J. 07662

[21] Appl. No.: 181,891

[22] Filed: Aug. 27, 1980

[51] Int. Cl.³ .............................................. A61M 5/00
[52] U.S. Cl. ............................. 128/218 M; 128/272.1
[58] Field of Search ...... 128/218 M, 218 D, 218 DA, 128/272.1, 213, 215, 216

[56] References Cited

U.S. PATENT DOCUMENTS

| | | | |
|---|---|---|---|
| 3,595,439 | 7/1971 | Newby et al. | 128/218 M X |
| 3,724,460 | 4/1973 | Gomez et al. | 128/218 M |
| 4,014,330 | 3/1977 | Genese | 128/218 M |
| 4,060,082 | 11/1977 | Lindberg et al. | 128/218 M |
| 4,171,698 | 10/1979 | Genese | 128/218 M |

*Primary Examiner*—John D. Yasko
*Attorney, Agent, or Firm*—Ralph R. Roberts

[57] ABSTRACT

This invention pertains to improvements in an intermixing syringe with isolation storage. The outer housing is similar to the conventional syringe and has a relatively constant diameter barrel with a hub at one end and wing portions at the other. A rigid insert is provided at the forward end of the housing, said insert made an air-tight fit by an O-ring. This insert includes a one-way valve to inhibit flow into the housing, a filter to remove all unwanted particles, a plurality of small passageways and a cone-like projection used to break a glass ampule in which the powder is stored prior to breaking and intermixing. A tubular member is slidably carried in this housing and contains the diluent. A plunger end closes this tubular member and a through passageway is closed at its lower end by a one-way valve that is closed when the plunger end is moved forwardly. A short passageway is also provided in the plunger end and provides flow communication for air from the outside into the tubular member. This passageway is closed by another one-way valve that is closed to the flow of diluent but open to an inflow of air when needed during the transfer of diluent to the housing.

12 Claims, 15 Drawing Figures

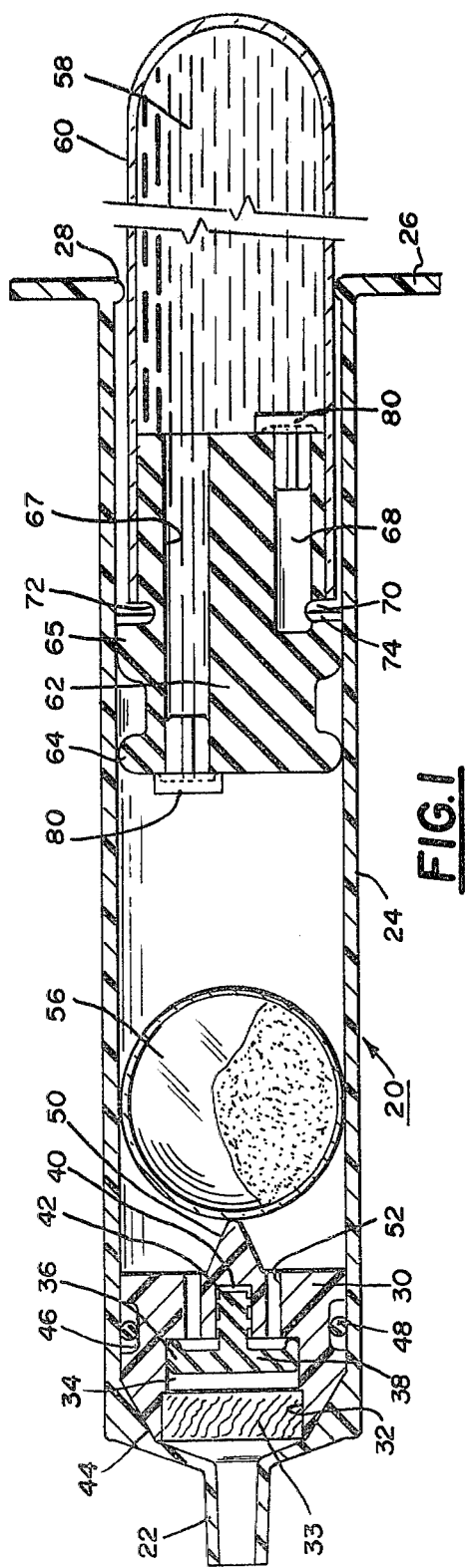

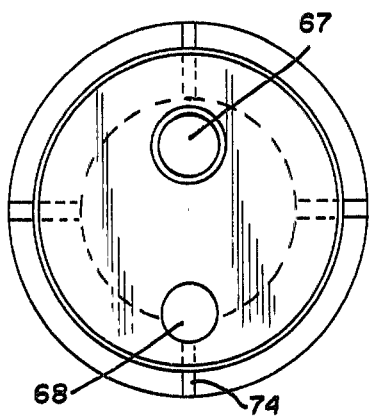
FIG.9
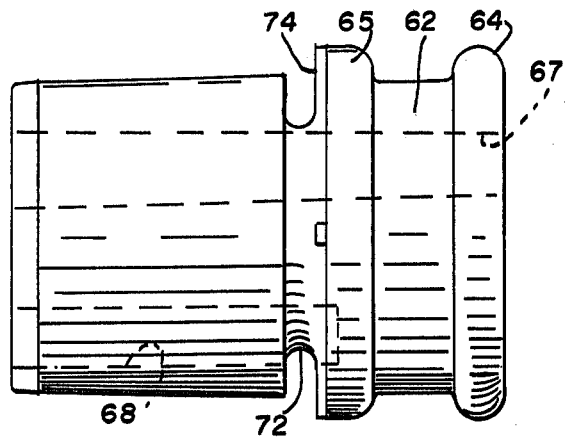
FIG.10
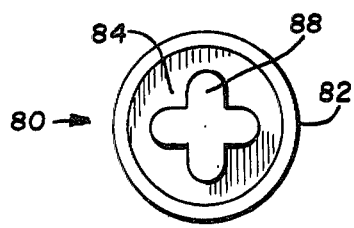
FIG.7  FIG.8
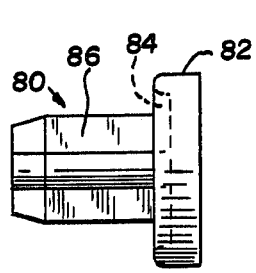
FIG.11
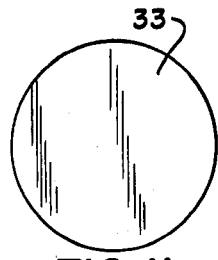
FIG.12
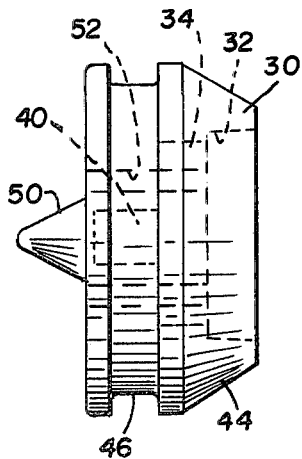
FIG.5
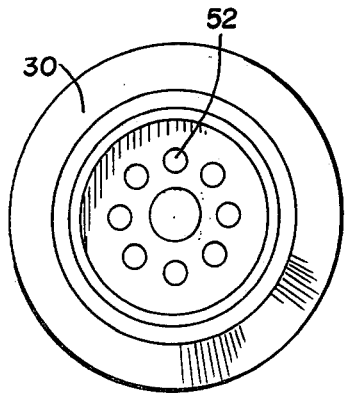
FIG.6
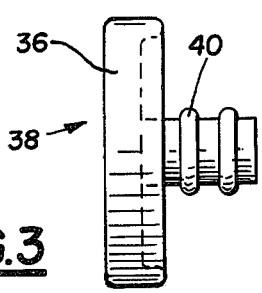
FIG.3
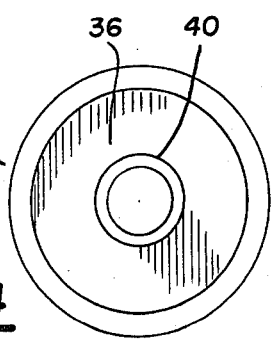
FIG.4

ISOLATION STORAGE AND INTERMIXING SYRINGE FOR MEDICANTS

BACKGROUND OF THE INVENTION

1. Field of the Invention

With reference to the classification of art as established in and by the United States Patent Office the present invention is believed to be found in the General Class entitled, "Surgery" (Class 128) and in the subclass therein entitled, "dosing devices—mixing syringes" (subclass 218 M).

2. Description of the Prior Art

The introduction of the hypodermic syringe and the like in which a movable plunger is used to draw fluid into the main barrel has been known for many years.

Intermixing syringes are, of course, not new and many attempts have been made to positively isolate powder from the diluent portion of the medicant during storage. Included in such proposed devices is U.S. Pat. No. 3,327,710 issued to FREEBERG on June 27, 1967. In this particular device the diluent is carried in one tube and the powder is carried in another tube. Means for puncturing of the barrier wall is provided to enable the diluent to be mixed with the powder.

Also of note is U.S. Pat. No. 3,534,734 to BUDRECK AS issued on Oct. 20, 1970; U.S. Pat. No. 3,489,147 to SHAW as issued on Jan. 13, 1970; U.S. Pat. No. 3,527,212 as issued to CLARK on Sept. 8, 1970; U.S. Pat. No. 3,303,846 as issued on Feb. 14, 1967; U.S. Pat. No. 3,542,023 as issued on Nov. 24, 1970 and U.S. Pat. No. 3,563,415 issued on Feb. 16, 1971, all three being issued to OGLE.

Also noted is U.S. Pat. No. 3,506,006 to LANGE as issued on Apr. 14, 1970; U.S. Pat. No. 3,405,712 issued to PIERICK on Oct. 15, 1968 and four patents to the Applicant, these being U.S. Pat. No. 3,464,412 as issued on Sept. 2, 1969; U.S. Pat. No. 3,566,859 as issued on Mar. 2, 1971; U.S. Pat. No. 3,659,749 as issued on May 2, 1972 and U.S. Pat. No. 3,678,930 as issued on July 25, 1972.

All of the above-noted patents are directed toward the intermixing of a powder and a diluent. However, these several devices, above-identified and others that are known, require a special syringe or a special container or both. The cost of establishing the necessary tooling and the associated production lines have deprived these devices of widespread acceptance. In the present invention the powder and the diluent are separately packaged. This powder is stored in a very thin glass ampule by common everyday techniques well known in the trade. The necessary sterilization procedures are also known and established. The plastic outer housing into which this ampule is contained and stored is commonly available and packaging of such an ampule in a sterile condition presents no problem.

The diluent is carried in a glass tube-like member which is slidable within an outer housing of plastic. This outer housing is conventional in shape and has a forward end with a hub provided for attachment of a hollow needle which is provided for injection. This device provides storage of the powder in a hermatically sealed glass ampule. The diluent is also enclosed in glass and is only moved into a mixing condition after the glass ampule has been broken. One-way valve means is provided to insure transfer and expelling of the mixed medicant. The mixed fluid is fed through a filter to remove any possible particles of glass or undissolved portions. An end insert secured in the front end of the outer housing provides a tapered projection by which the glass ampule is broken and has small passageways which exclude the larger glass portions before filtration.

SUMMARY OF THE INVENTION

This invention may be summarized, at least in part, with reference to its objects.

It is an object of this invention to provide, and it does provide, a simple and inexpensive isolation and intermixing chamber in which powder and an associated diluent are each retained in separate storage compartments. The powder is stored in the round glass ampule and the diluent is stored in the glass retainer closed by the plunger end.

It is a further object of this invention to provide, and it does provide, an inexpensive isolating and intermixing chamber wherein powder and a diluent are separately encased in glass retained in a plastic outer housing conventional in design and use and having an open rear end and a forward end with a hub and passageway on which is mounted a hollow needle. Within this outer housing and at the forward end is a filter enclosed by an end insert which is provided with an ampule breaking assist. The diluent is carried within a glass tubular member and the forward end carries a plunger adapted to effect a fluid transfer with and by negative pressure.

In brief, this invention provides an outer housing of plastic and essentially with the configuration of a syringe. Within this housing and at the forward end is carried an insert of rigid plastic having a recess which secures a filter. A one-way valve and a plurality of fluid passageways are provided in this insert. A shaped projection is also provided on said insert. A glass ampule carries the powder and is crushed at time of intermixing. The diluent is carried in a closed glass tubular member. This tubular member is closed by a plunger having one-way valves and an air passageway for admitting air during expulsion.

In addition to the above summary the following disclosure is detailed to insure adequacy and aid in understanding of the invention. This disclosure, however, is not intended to cover each new inventive concept therein no matter how it may later be disguised by variations in form or additions of further improvements. For this reason there has been chosen a specific embodiment of the isolation storage and intermixing chamber as adopted for use with a conventional syringe. This specific embodiment has been chosen for the purposes of illustration and description as shown in the accompanying drawing wherein:

BRIEF DESCRIPTION OF THE DRAWINGS

FIG. 1 represents a sectional side view, partly diagrammatic, of the preferred embodiment and showing the several components arranged in a storage condition;

FIG. 2 represents an expanded isometric view, partly diagrammatic, and showing the major components as aligned for assembly;

FIG. 3 represents, in an enlarged scale, the side view of a flapper valve that is utilized to prevent fugitive flow to the filter;

FIG. 4 represents a plan view of the flapper valve of FIG. 3, this view taken on the line 4—4 thereof and looking in the direction of the arrows;

FIG. 5 represents a side view of an end insert within the outer barrel, this insert having a ball engaging and breaking conical protrusion and recess for a filter;

FIG. 6 represents a plan view of the end insert of FIG. 5, this view taken on the line 6—6 thereof and looking in the direction of the arrows;

FIG. 7 represents a plan view of a small one-way valve closure used with the plunger end;

FIG. 8 represents a side view of the valve closure of FIG. 7, this view taken on the line 8—8 thereof and looking in the direction of the arrows;

FIG. 9 represents a plan view of the plunger and closure as mountable in the glass test tube-like member;

FIG. 10 represents a side view of the plunger end closure of FIG. 9, this view taken on the line 10—10 thereof and looking in the direction of the arrows;

FIG. 11 represents a plan view of the disk-like assembly of the filter component provided and mountable in a recess in the end insert;

FIG. 12 represents a side view of the filter component of FIG. 11, this view taken on the line 12—12 thereof and looking in the direction of the arrows;

In the following description and in the claims various details are identified by specific names for convenience. These names are intended to be generic in their application. Corresponding reference characters refer to like members throughout the several figures of the drawings.

DESCRIPTION OF THE PREFERRED EMBODIMENT

Figure 13:
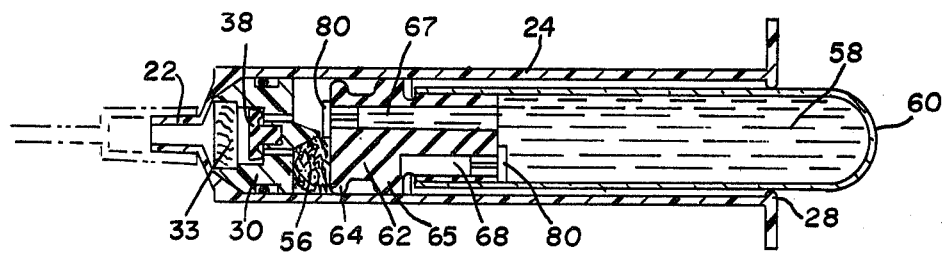
FIG. 13 represents a sectional side view as in FIG. 1 but with the plunger and particularly the inner end moved inwardly or forwardly sufficiently to fracture the glass ampule carrying and enclosing the powder.

Referring next to the drawings, there is shown the preferred embodiment of this intermixing syringe. In FIGS. 1 through 12 the several components are shown in an assembled and also in a separate array. In FIGS. 1 and 2 the outer housing generally identified as 20 is shown. This housing is preferably of substantially rigid plastic. This housing is open at both ends and is conventional with a hub end 22 having an expelling conduit therethrough. On this hub, which is conventionally slightly tapered, is mounted a hollow needle, not shown. This housing includes a central tubular portion 74 which terminates at a large left end which has wing portions 26 extending therefrom. A retaining lip 28 is also preferably provided at this larger end. This retaining lip 28 is usually provided so as to prevent unwanted dislodgement of the plunger when drawn to its outward condition and position.

Mounted in the forward end of housing 20 is an insert generally identified as 30. The forward or rightwardly shaped end is provided with a circular recess 32 and in this recess is mounted a filter 33. Inwardly of this recess is another recess 34 which is sized to receive the larger disk portion 36 of a flapper valve member generally identified as 38. This recess 34 enters or is a part of a stem recess 40 sized to tightly receive and retain a stem portion 42 of the flapper valve member 38. This end insert has a bevel 44 which is a snug fit in the forward end of the outer housing 20. To the left of the beveled end 44 is a groove 46 in which is mounted an O-ring 48. The left face of this insert 30 is formed with a tapered or cone-like projection 50. Also formed in this insert and immediately outwardly of the cone-like projection 50 are a plurality of through and small conduits 52 which carry the mixed fluid to the flapper valve 38.

In the assembly of FIGS. 1 and 2 there is shown a glass ampule 56 which is of thin glass and encloses the powder to be mixed with the diluent to be later identified. This glass ampule may or may not be spherical in shape and may have a tip portion that is closed at the time of sealing the powder in the ampule. The size of the ampule is a matter of choice and capacity requirement. This ampule is freely slidable within the outer housing 20.

Fluid or diluent 58 may be water or other fluid to be mixed with the powder in the ampule at the time of use. This diluent is carried in a glass tubular member 60 which is closed at its outer end and is open at its inner or right end. The length and capacity of this diluent tubular carrier is a matter of selection but the diameter is disposed to be a freely slidable fit within the retaining inward lip 28 of the housing 20. The open end of member 60 is closed by a plunger end 62.

This plunger end 62 is preferably made of a rubber or rubberlike material which is molded to the desired shape. This material is acceptable for storage of the diluent and is sufficiently resilient to be pushed by the lip 28 while the outward rib portions 64 and 65 engage and provide a seal of the plunger in the central tubular portion 24 of the housing 20. As seen in FIG. 1, and in more detail in FIGS. 9 and 10, this plunger end also includes longitudinal passageways 67 and 68. The passageway 67 is through the entire plunger end 62 while passageway 68 terminates about at the second outward rib portion 65. A short outwardly directed passageway 70 is in flow communication with the passageway 68 and the exterior of the plunger end 62. A circumferential groove 72 is molded in this plunger end. The mounting of the large open end of the tubular member 60 on the plunger end 62 is controlled by stop tabs 74 which are depicted as four in number but may be as few as three and more than four.

In the plunger end 62 is mounted one-way valve closure members 80. These are two members 80 of like size and shape depicted but these may be dissimilar in size if desired. These one-way valve closure members are shown in greater detail in FIGS. 7 and 8 and are made of a rubber-like or rubber material usually molded to shape. As in the case of the plunger end 62 each one-way valve member is of material that is acceptable for the storage of the diluent used. This molded shape includes a disk-like end 82 which has shallow inner recess portion 84. A shank 86 has flute portions 88 which are shown as four in number but may be as few as three and more than four. These flute portions allow a secure mounting while permitting air flow along the flutes.

ASSEMBLY AND USE

It is assumed that the intermixing syringe will be assembled, stored and transported while in a sterile condition. The assembly will be under antiseptic conditions that are easily provided. The storage of the powder or medicant within the glass ampule 56 is by the drug company or supplier and is received in a sterile condition. The filter 33 is mounted in recess 32 after the one-way flapper valve member 38 is mounted in recess 34 and stem recess 40. The disk portion 36 is greater than or extends beyond the pattern of conduits 52. In a mounted condition the flapper valve 38 and filter 33 are retained when the end insert 30 is secured in the forward portion of the housing 20.

The diluent 58 is poured into the upturned glass tubular member 60. The plunger end 62 is assembled with a one-way valve closure member 80 in the passageway 67 and a one-way valve in the passageway 68. The assembled plunger end is now inserted into the large end of the glass tubular member 60 until the large end engages the stop tabs 74. The one-way valve 80 in passageway 67 allows air in the upper end of the glass tubular member 60 to escape during assembly.

The glass ampule 56 is now placed within the housing 20 and the plunger end 62 is brought to the housing 20. The end 62 is now pushed by retaining lip 28 and the outward rib portions 64 and 65 engage and slide within the inner diameter of the central tubular portion 24 and is advanced to a storage condition such as in FIG. 1. The flapper valve member 38 allows air compressed by the advancing plunger end 62 to escape from the interior of the housing 20.

When it is desired to intermix the components, the protective sheath or package wrapping, not shown, is removed. A hollow needle of conventional design may be mounted on the hub end 22 and the glass tubular member 60 is moved forwardly causing the glass ampule 56 to be broken. The ampule 56 is broken sufficiently to allow the powdered material therein to be exposed for mixing. It is to be noted that the plurality of conduits 52 are made sufficiently small so that the larger glass particles are prevented from passing therethrough. The filter 33 may include facing and protective metal mesh disk if desired. The crushing of the ampule is shown in FIG. 13.

Figure 14:
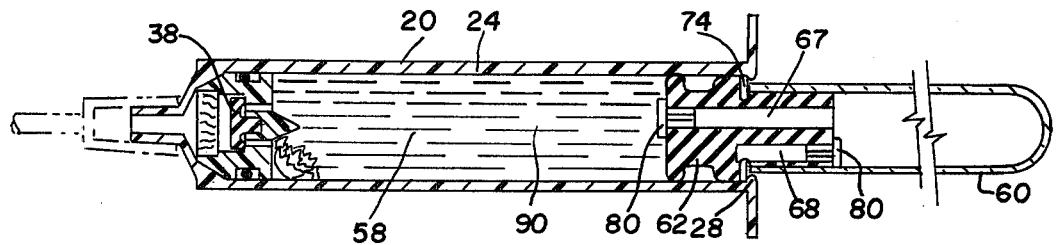
FIG. 14 represents a sectional view of the apparatus of FIG. 13 with the plunger moved to its outer position whereat the fluid in the plunger has been transferred to the syringe barrel and mixing may be made.

In FIG. 14 the plunger end 62 is shown as drawn outwardly to the retaining lip 28. Stop tabs 74 may engage the lip 28 to provide the desired resistance to outward movement. The diluent 58 is caused to be transferred by negative pressure from the glass tubular member 60 to the central portion of the housing 20. At this condition the intermixing is made with this medicant being identified as 90. Normally the turbulance by and with the transfer is sufficient to achieve the intermix but further mixing may be made with a shaking action. During the movement of the plunger end 62 to its rear or outer position from the crushing condition of FIG. 13 the flapper valve 38 is closed. The one-way valve closure member 80 in passageway 68 is closed while that one-way valve 80 in passageway 67 opens. This opening of the passageway to the flow of diluent 58 allows the diluent to be transferred to the tubular portion 24 of the housing 20.

Figure 15:
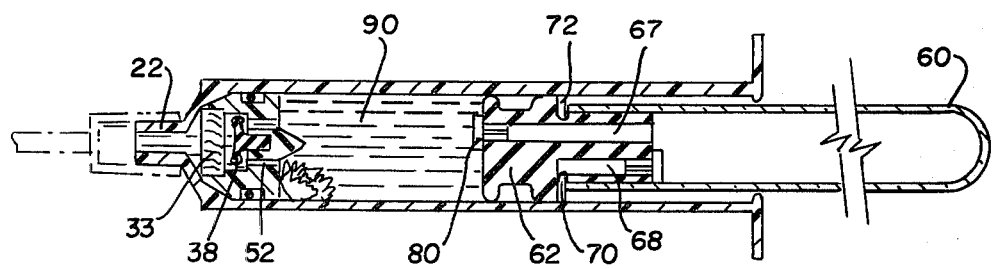
FIG. 15 shows the syringe of FIG. 14 with the mixed fluid being expelled from the syringe after passing through the filter.

In FIG. 15 the expelling of the mixed medicant 90 is made in the usual manner. As the plunger end 62 is advanced forwardly the one-way valve 80 in passageway 67 is closed. The flapper valve 38 opens sufficiently for the mixed fluid 90 to pass through small conduits 52 and filter 33 to and through the expelling conduit in the hub end 22.

It is to be noted that the one-way valve 80 in passageway 68 is open to admit air to the interior of the glass tubular member 60. The air to the interior of this member 60 allows the transfer of diluent 58. The needed air flows down the exterior of the member 60 thence into groove 72 and through short passageway 70. It is to be noted that the passageway 68 may be provided with a tubular extension and a one-way valve to insure that entering air is carried to the upper end of the tubular member 60.

The above assemblage is adapted for high speed production while providing antiseptic conditions. Many, if not all packaging is contemplated to be made with and by mechanical devices. Final transport is also contemplated to be in a sterile wrapper. Any fugitive moisture flow through the plunger end 62 is prevented from contact with the powder until mixing since the powder is stored in the glass ampule 56. Although shown with extending wing portions 26 that are provided as assists to manipulation, this is not to preclude their elimination. Also, the glass tubular member 60 for the diluent 58 may be shaped to suit the particular product and use. The diluent may be stored in other than glass if acceptable to the regulatory agency or agencies that approve the package. The glass ampule 56 usually contains a medicant powder but this is not to preclude the enclosed portion being fluid or paste. It is important that intermixing be achievable within the syringe, substantially in the manner above described.

It is contemplated that a safety filter 33 is, of course, porous and is provided in the syringe to prevent passage into the needle of any material larger than the filter pass capacity. This filter has the inhibiting ability to prevent the passage of materials larger than two or five microns and this small size will certainly exclude the smallest potential particle of glass which is ten to twenty-five micron from entering the syringe.

Terms such as "up", "down", "bottom", "top", "in", "out" and the like are applicable to the embodiment shown and described in conjunction with the drawing. These terms are merely for the purposes of description and do not necessarily apply to the position in which the intermixing syringe may be constructed or used.

While a particular embodiment of this syringe has been shown and described the invention is not limited thereto and protection is sought to the broadest extent the prior art allows.

What is claimed is:

1. An isolation storage and intermixing syringe for medicants for use when and where positive isolation and sterility of two components are to be maintained until the time of intermixing and use, said intermixing syringe including:
   (a) an outer housing of a rigid composition, said housing having an intermediate portion with a relatively constant diameter and with a substantially closed front end with an expelling aperture therethrough, the rear end of this housing having an opening substantially the size of the inner diameter provided in the intermediate portion of the housing;
   (b) a rigid insert provided in the forward end of the housing and adapted to be a snug fit in said forward end, said insert having a recess and a plurality of through conduits from an inner face to the recess;
   (c) a flapper valve member providing a one-way valve means and mounted in said recess to inhibit flow into the housing while permitting flow from said housing to and through the conduits;
   (d) a filter disposed in said recess and disposed to filter fluid flow from the housing interior to and through the expelling aperture;

(e) a rigid cone-like projection provided on the insert and disposed so as to extend into the intermediate housing portion;

(f) a glass ampule freely slidable in the housing and adapted to retain the medicant portion in a sterile and unaffected condition until broken for intermixing;

(g) a rigid tubular member slidably carried in the housing and adapted to retain a determined quantity of diluent, this tubular member having a closed rear end and an open front end of a size substantially at the maximum diameter of configuration;

(h) a plunger end mountable in the open end of the tubular member and including at least one outwardly extending rib to provide a sliding seal of the plunger end in the interior diameter of the intermediate portion of the housing, this plunger end also having a through longitudinal passageway and an incomplete longitudinal passageway extending from the inner end of the mounted plunger end to an outwardly directed conduit connecting to an air pathway to the outer portion of the housing, this plunger end made of a resilient material;

(i) a one-way valve means closing the through passageway in the plunger end to flow of fluid from the housing to the tubular member through the plunger end while said valve is open to flow from the tubular member to the housing;

(j) a one-way valve means closing the incomplete passageway in the plunger end to a flow of stored diluent in the tubular member and with the forward movement of the plunger end on the tubular member the glass ampule is caused to fracture and expose its contents, and the outward movement of the tubular member causes a reduced pressure to be provided in the housing and under this influence of reduced pressure the diluent is transferred from the tubular member to the housing while the air flows into said tubular member during transfer, the transfer and shaking inducing the desired intermix, after which the plunger end is moved forwardly toward the insert to cause the intermixed fluid medicant to be expelled through the insert, the filter and from the housing.

2. An isolation storage and intermixing syringe as in claim 1 in which the rigid insert has a resilient sealing means on its outer diameter, said sealing means inhibiting the passage of air thereby.

3. An isolation storage and intermixing syringe as in claim 1 in which the housing is molded of rigid, substantially clear plastic with the forward portion formed with a conventionally tapered hub on which may be removably mounted a hollow needle.

4. An isolation storage and intermixing syringe as in claim 3 in which the housing is provided with extending wing portions and the rear end of the housing is formed with an inward retaining lip.

5. An isolation storage and intermixing syringe as in claim 1 in which the rigid insert mounted in the forward end of the housing is secured within the interior of said housing by an O-ring carried in a peripherial groove formed in the insert and providing means to inhibit the passage of air thereby, said insert forwardly of this O-ring formed with a taper adapted to mate with the inner contour of the housing.

6. An isolation storage and intermixing syringe as in claim 5 in which the flapper valve mounted in this recess has a stem portion that is an interference fit in a reduced recess portion and the flapper valve is of resilient material having a disk portion secured to the stem, this disk portion having a rim adapted to engage a wall portion of the recess to provide the desired one-way valve action.

7. An isolation storage and intermixing syringe as in claim 6 in which the filter is carried in the recess and is adjacent to the flapper valve, this filter disposed to filter the intermixed fluid just prior to the travel through the expelling aperture.

8. An isolation storage and intermixing syringe as in claim 7 in which the plurality of conduits found in the insert are small and are disposed outside the cone-like projection and the flapper valve is disposed to cover the exiting ends of said conduits.

9. An isolation storage and intermixing syringe as in claim 1 in which the tubular member is a glass member.

10. An isolation storage and intermixing syringe as in claim 9 in which the plunger end is made with a plurality of outwardly extending ribs and the inserted end of the plunger end is insertable only to a circumferential groove which is adjacent intermittently formed stop tabs molded as a part of the plunger end.

11. An isolation storage and intermixing syringe as in claim 10 in which the one-way valve means is a resilient plug having a disk-like end with an outer circumferential rim portion outwardly disposed from a shallow recess portion, this disk-like portion secured to a fluted shank, these flutes providing flow pathways when the disk-like portion is deflected to and into an open condition.

12. An isolation storage and intermixing syringe as in claim 11 in which the one-way valve means in the plunger end are like moldings of a rubber-like material.

* * * * *